US012685543B2

(12) United States Patent
Gleason et al.

(10) Patent No.: US 12,685,543 B2
(45) **Date of Patent: \*Jul. 21, 2026**

(54) PERCUTANEOUS DISCECTOMY KIT AND METHOD

(71) Applicant: Spineology Inc., St. Paul, MN (US)

(72) Inventors: Joseph Gleason, Eagan, MN (US); Garrett Ganske, Lino Lakes, MN (US); Dan McPhillips, Ham Lake, MN (US); Craig Bourgeault, St. Louis Park, MN (US)

(73) Assignee: Spineology Inc., St. Paul, MN (US)

( * ) Notice: Subject to any disclaimer, the term of this patent is extended or adjusted under 35 U.S.C. 154(b) by 68 days.

This patent is subject to a terminal disclaimer.

(21) Appl. No.: 18/951,258

(22) Filed: Nov. 18, 2024

(65) Prior Publication Data

US 2025/0072909 A1 Mar. 6, 2025

Related U.S. Application Data

(63) Continuation of application No. 18/084,479, filed on Dec. 19, 2022, now Pat. No. 12,144,514, which is a continuation of application No. 17/027,631, filed on Sep. 21, 2020, now Pat. No. 11,529,149.

(60) Provisional application No. 62/903,505, filed on Sep. 20, 2019, provisional application No. 62/903,458, filed on Sep. 20, 2019, provisional application No.
(Continued)

(51) Int. Cl.
| *A61B 17/16* | (2006.01) |
| *A61B 17/00* | (2006.01) |
| *A61B 17/3209* | (2006.01) |

| *A61B 17/34* | (2006.01) |
| *A61B 17/92* | (2006.01) |
| *A61B 90/00* | (2016.01) |
(Continued)

(52) U.S. Cl.
CPC .... *A61B 17/1671* (2013.01); *A61B 17/00234* (2013.01); *A61B 17/3209* (2013.01); *A61B 17/3423* (2013.01); *A61B 17/92* (2013.01); *A61B 90/06* (2016.02); *A61F 2/4611* (2013.01); *A61B 6/481* (2013.01); *A61B 2017/00261* (2013.01); *A61B 2017/922* (2013.01); *A61B 2090/062* (2016.02)

(58) Field of Classification Search
CPC .................................................. A61B 17/1671
See application file for complete search history.

(56) References Cited

U.S. PATENT DOCUMENTS

| 9,232,906 | B2 * | 1/2016 | Wolf, II ............... A61B 5/4836 |
| 11,529,149 | B2 * | 12/2022 | Gleason ............... A61F 2/4611 |
(Continued)

*Primary Examiner* — Christian A Sevilla
(74) *Attorney, Agent, or Firm* — Spineology Inc.

(57) ABSTRACT

A method for performing percutaneous spinal interbody fusion on a spine of a patient can include inserting without direct visualization a neuro-monitoring dilating probe into the patient, performing neuro-monitoring via the neuro-monitoring dilating probe, advancing the neuro-monitoring dilating probe into a disc space, passing a second dilator over the neuro-monitoring dilating probe, and advancing the second dilator into the disc space. A kit for performing percutaneous spinal interbody fusion can include a neuro-monitoring dilating probe, a second dilator, a tissue removal tool, an access portal comprising an adjustable depth stop, and a discectomy verification device.

20 Claims, 15 Drawing Sheets

Related U.S. Application Data

62/903,480, filed on Sep. 20, 2019, provisional application No. 62/903,492, filed on Sep. 20, 2019, provisional application No. 62/903,549, filed on Sep. 20, 2019.

(51) Int. Cl.
*A61F 2/46* (2006.01)
*A61B 6/00* (2006.01)

(56) References Cited

U.S. PATENT DOCUMENTS

| | | | | |
|---|---|---|---|---|
| 12,144,514 B2 * | 11/2024 | Gleason | ............... | A61B 5/6852 |
| 2003/0083688 A1 * | 5/2003 | Simonson | ............ | A61B 17/025 |
| | | | | 606/191 |
| 2008/0183190 A1 * | 7/2008 | Adcox | .................. | G16H 30/40 |
| | | | | 606/130 |

* cited by examiner

60

306
305
312
300
304
304
313
302
310

308
314
309
313

316
304
316

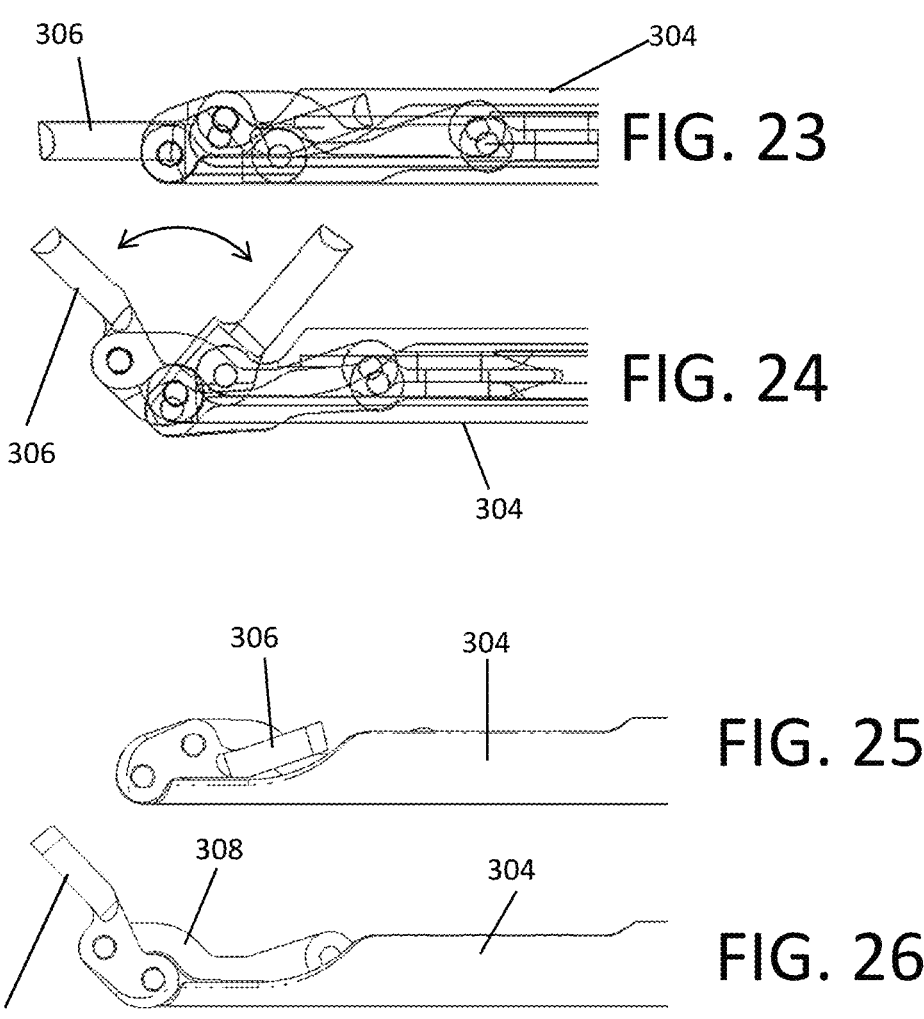
FIG. 23
FIG. 24
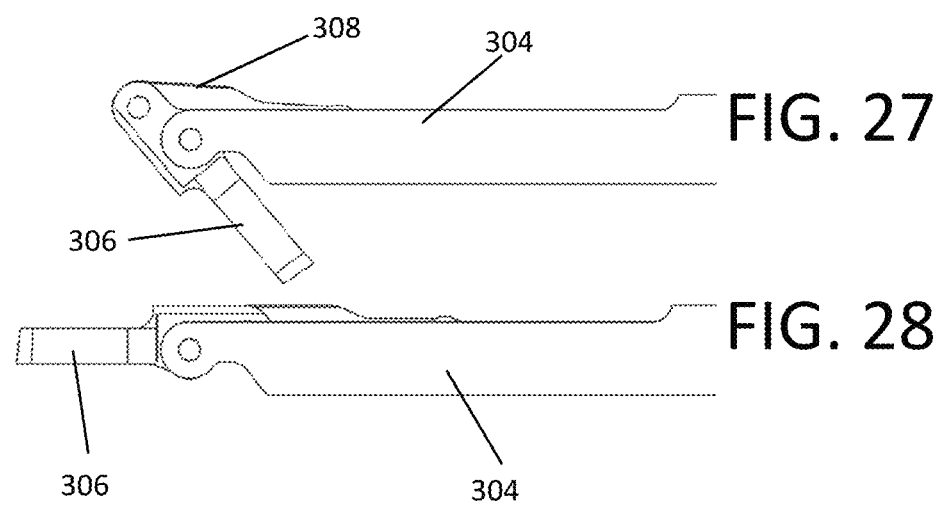
FIG. 25
FIG. 26
FIG. 27
FIG. 28

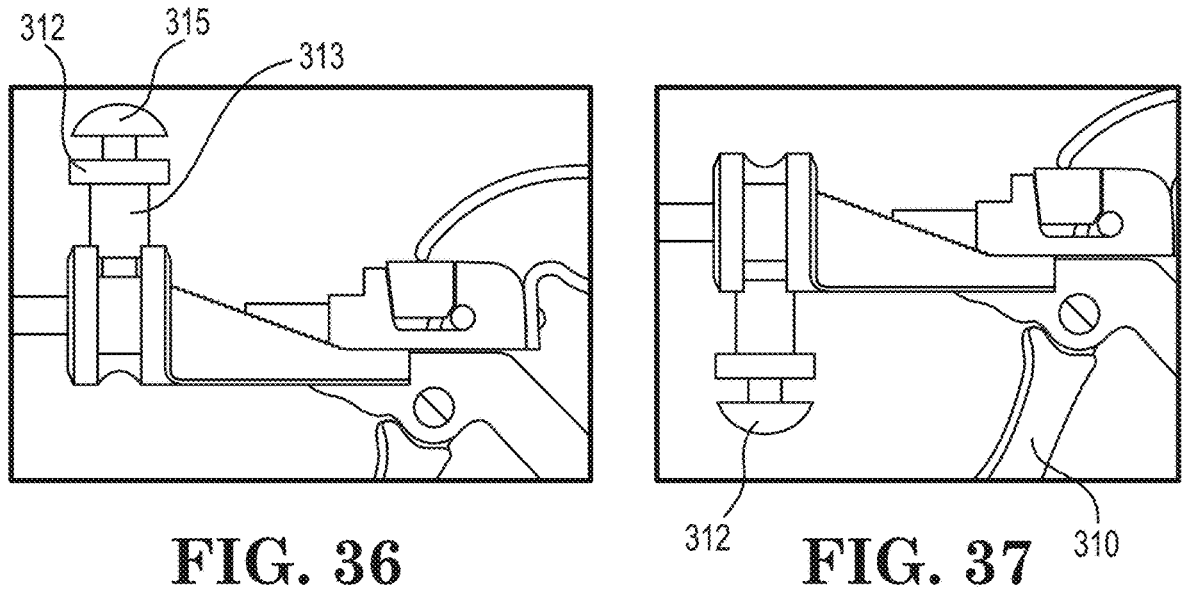
FIG. 36          FIG. 37
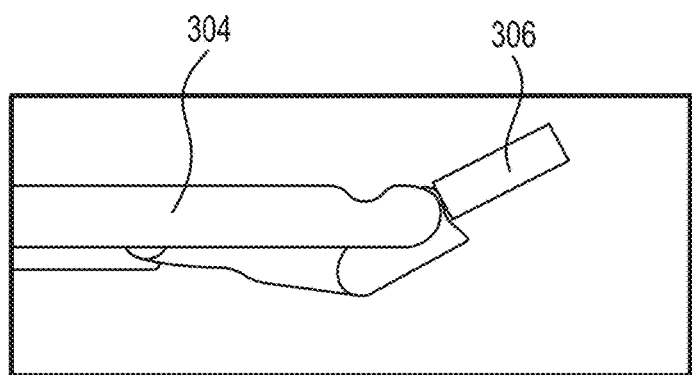
FIG. 38
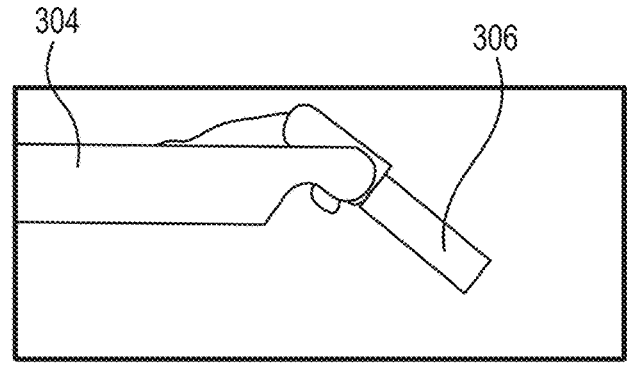
FIG. 39

PERCUTANEOUS DISCECTOMY KIT AND METHOD

PRIORITY

This application is a continuation of U.S. application Ser. No. 18/084,479, filed Dec. 19, 2022, which is a continuation of U.S. application Ser. No. 17/027,631, filed Sep. 21, 2020, now U.S. Pat. No. 11,529,149 B2, which claims the benefit of U.S. Provisional Application Ser. No. 62/903,549, filed on Sep. 20, 2019, U.S. Provisional Application Ser. No. 62/903, 458, filed on Sep. 20, 2019, U.S. Provisional Application Ser. No. 62/903,480, filed on Sep. 20, 2019, U.S. Provisional Application Ser. No. 62/903,492, filed on Sep. 20, 2019, and U.S. Provisional Application Ser. No. 62/903,505, filed on Sep. 20, 2019. Each of the foregoing applications is hereby incorporated herein by reference in its entirety.

FIELD

The present invention generally relates to a kit of instruments and a method for performing a percutaneous discectomy. More particularly, the present invention relates to instruments and methods for performing an efficient and thorough intervertebral discectomy.

BACKGROUND

It is recognized that the spinal disc consists of three parts: first, the nucleus, a central portion that is a compression-resisting cushion; second, the annulus, a peripheral rim portion that is a tension-resisting hoop; and third, the end plates, the superior and inferior borders of the disc, consisting of the upper and lower surfaces of the vertebral body bones adjacent to the disc. Many studies have concluded that mechanical back pain is the most common and costly musculoskeletal condition affecting middle-aged humans in modern societies. Mechanical back pain may be caused by several factors, but overwhelming evidence suggests that degeneration of the spinal intervertebral disc, such as may be caused by Degenerative Disc Disease (DDD) is the most common condition causing back pain symptoms.

Like many other areas of surgery, spine surgery has become less invasive as smaller, more precise technology develops. However, all minimally invasive spinal procedures still require a surgical access opening that is as large as the device to be implanted. Generally speaking, the access aperture in minimally invasive procedures is at least 15-30 mm in diameter. Also, because minimally invasive procedures require direct visualization, the surgeon may need to cut bone and must significantly retract soft tissues and the nerve root, potentially causing nerve root injury or persistent post-operative pain.

By contrast, percutaneous surgery is done using x-ray visualization and image guidance and as such does not require resection of bony or soft tissue for direct visualization of the disc. Further, the incision is generally in the range of about 10 mm, much smaller than the access aperture in MIS procedures. Thus, percutaneous surgery results in a dramatic reduction in morbidity rates and more rapid recovery, both of which leading to significantly shorter hospitalization times.

U.S. Pat. Nos. 6,558,383 and 7,087,058 to Cragg describe a percutaneous method of fusing the lumbo-sacral region of the spine from an axial approach. The method and system described by Cragg are limited to fusing either the L5-S1 or the L4-L5-S1 motion segments using a rigid device and are further limited to an axial approach. Further, although Cragg describes the method as being percutaneous, the method still requires an access opening of at least 22 mm to accommodate the implant. The larger a surgical exposure is, the greater the likelihood of attendant bleeding and injury to local muscular, ligamentous, vascular and nervous tissues and in the lumbar region, the bowels may also be damaged Existing percutaneous discectomy systems and methods typically require the following instruments to create access to the disc space: a neuro-monitoring probe, exchange tube, guide pin, a first dilator and a second dilator. Presently, in general, percutaneous access to the disc is accomplished by using a guide pin and imaging to mark the skin and determine an incision point; inserting a neuro-monitoring probe into an exchange tube and to create an assembly; inserting the neuro-monitoring/exchange tube assembly into the disc space while imaging to determine a safe path and trajectory; removing the neuro-monitoring probe, while leaving the exchange tube in the disc space; inserting a guide pin through the exchange tube into the disc space; removing the exchange tube; advancing the guide pin to the middle of the disc while imaging to determine placement; place the first dilator over the guide pin while imaging; remove the guide pin; place the second dilator over the first dilator while imaging; remove the first dilator; place an access portal into the site and then proceed with discectomy instruments.

Any procedure that would more easily, and/or more effectively, and/or more safely treat degenerative disc disease would be useful in the management of hundreds of thousands of suffering individuals. The current invention is an improvement to current systems and methods of performing spine surgery because it enables surgeons to finally perform a true percutaneous discectomy at all levels of the spine

SUMMARY

The present invention, according to certain embodiments, is a system and method for performing an efficient and thorough percutaneous discectomy. In an embodiment, a percutaneous incision, that is a small stab wound, no more than approximately 10 mm in length is made into the patient. A stimulated combination neuro-monitoring dilating probe is passed through an approximately 10 mm or less skin incision and into a patient's disc space to establish a safe path and trajectory through Kambin's Triangle. Once a neuro-monitoring dilating probe is in the disc space, a second dilator is placed over the neuro-monitoring dilating probe and impacted into the disc space. Neuro-monitoring dilating probe may then be removed. An access portal optionally combined with a force dissipation device may then be placed over the second dilator and into the disc space. The second dilator is removed and then discectomy instruments may be placed through the access portal to perform the discectomy.

The detailed technology and preferred embodiments implemented for the subject invention are described in the following paragraphs accompanying the appended drawings for people skilled in this field to well appreciate the features of the claimed invention. It is understood that the features mentioned hereinbefore and those to be commented on hereinafter may be used not only in the specified combinations, but also in other combinations or in isolation, without departing from the scope of the present invention.

BRIEF DESCRIPTION OF THE DRAWINGS

FIG. 23 is a side view of a distal end portion of a shaper in accordance with certain embodiments of the present invention.

FIG. 24 is a side view of a distal end portion of a shaper in accordance with certain embodiments of the present invention.

FIG. 25 is a side view of a distal end portion of a shaper in accordance with certain embodiments of the present invention.

FIG. 26 is a side view of a distal end portion of a shaper in accordance with certain embodiments of the present invention.

FIG. 27 is a side view of a distal end portion of a shaper in accordance with certain embodiments of the present invention.

FIG. 28 is a side view of a distal end portion of a shaper in accordance with certain embodiments of the present invention.

FIG. 36 is a side view of a proximal end portion of a shaper in accordance with certain embodiments of the present invention.

FIG. 37 is a side view of a proximal end portion of a shaper in accordance with certain embodiments of the present invention.

FIG. 38 is a side view of a distal end portion of a shaper in accordance with certain embodiments of the present invention.

FIG. 39 is a side view of a distal end portion of a shaper in accordance with certain embodiments of the present invention.

Figure 1:
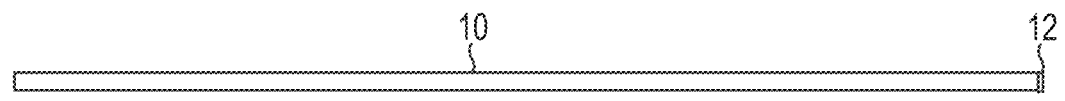
FIG. 1 is a top view of an exchange tube in accordance with certain embodiments of the present invention.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the spirit and scope of the invention as defined by the appended claims. For illustrative purposes, cross-hatching, dashing or shading in the figures is provided to demonstrate sealed portions and/or integrated regions or devices for the package.

DETAILED DESCRIPTION

In the following descriptions, the present invention will be explained with reference to example embodiments thereof. However, these embodiments are not intended to limit the present invention to any specific example, embodiment, environment, applications or particular implementations described in these embodiments. Therefore, description of these embodiments is only for purpose of illustration rather than to limit the present invention. It should be appreciated that, in the following embodiments and the attached drawings, elements unrelated to the present invention are omitted from depiction; and dimensional relationships among individual elements in the attached drawings are illustrated only for ease of understanding, but not to limit the actual scale.

The present invention reduces steps, instruments and imaging requirements from currently available discectomy methods and includes a comprehensive system and method for performing a true percutaneous discectomy. In an embodiment, the system may include a neural stimulating and dilating probe, a second dilator, an access portal, disc removal/cavity creation tool(s), and a discectomy evaluation device.

According to the present invention, percutaneous interbody spinal fusion (e.g. of a human or other mammal) is performed under indirect visualization using x-ray or other imaging visualization without any direct visualization. Because neural tissue cannot be seen on x-ray, there is a need for active neural monitoring to ensure there is no injury to the surrounding nerves during the procedure. There are two types of monitoring that are generally used in spine surgery: Electromyography (EMG) and Somatosenory Evoked Potential (SEP). When using neural monitoring in the spine, the surgeon is evaluating nerve potential, that is, its ability to react, and checking for evoked responses. An instrument, such as a neural stimulating component, is used to mechanically manipulate or electrically stimulate the nerve in order to evoke a response. The main difference between EMG and SEP is that EMG looks at muscle responses and therefore is used for tracking nerve root response and SEP is used for dorsal column monitoring or spinal cord responses.

In an embodiment of the present invention, an incision point may be located using anterior-posterior (AP) imaging. A guide pin may be placed on the skin with a guide pin tip located at the junction of the ipsilateral border of the spine and the superior endplate of the inferior vertebral body. Said junction may be marked on the patient's skin with a marker. A guide pin may then be placed on the skin with the tip located at the junction of the contralateral border of the spine and the superior endplate of the inferior vertebral body. This junction may then be marked on the patient's skin with a marker.

Next, a guide pin may be placed flat on the patient's skin and the guide pin marked with the distance from point A to B. Then this distance (point A to B) may be transferred laterally from the ipsilateral edge of the vertebral body and said point may be marked on the patient's skin. This location indicates the approximate incision location.

Then the guide pin tip is placed at the proposed incision point. A lateral image may be taken to confirm that the incision point is in line with the disc. In an embodiment, a generally less than 10 mm medial-lateral incision may then be made. A medial-lateral incision facilitates trajectory corrections and ability to perform a thorough discectomy.

Figure 17:
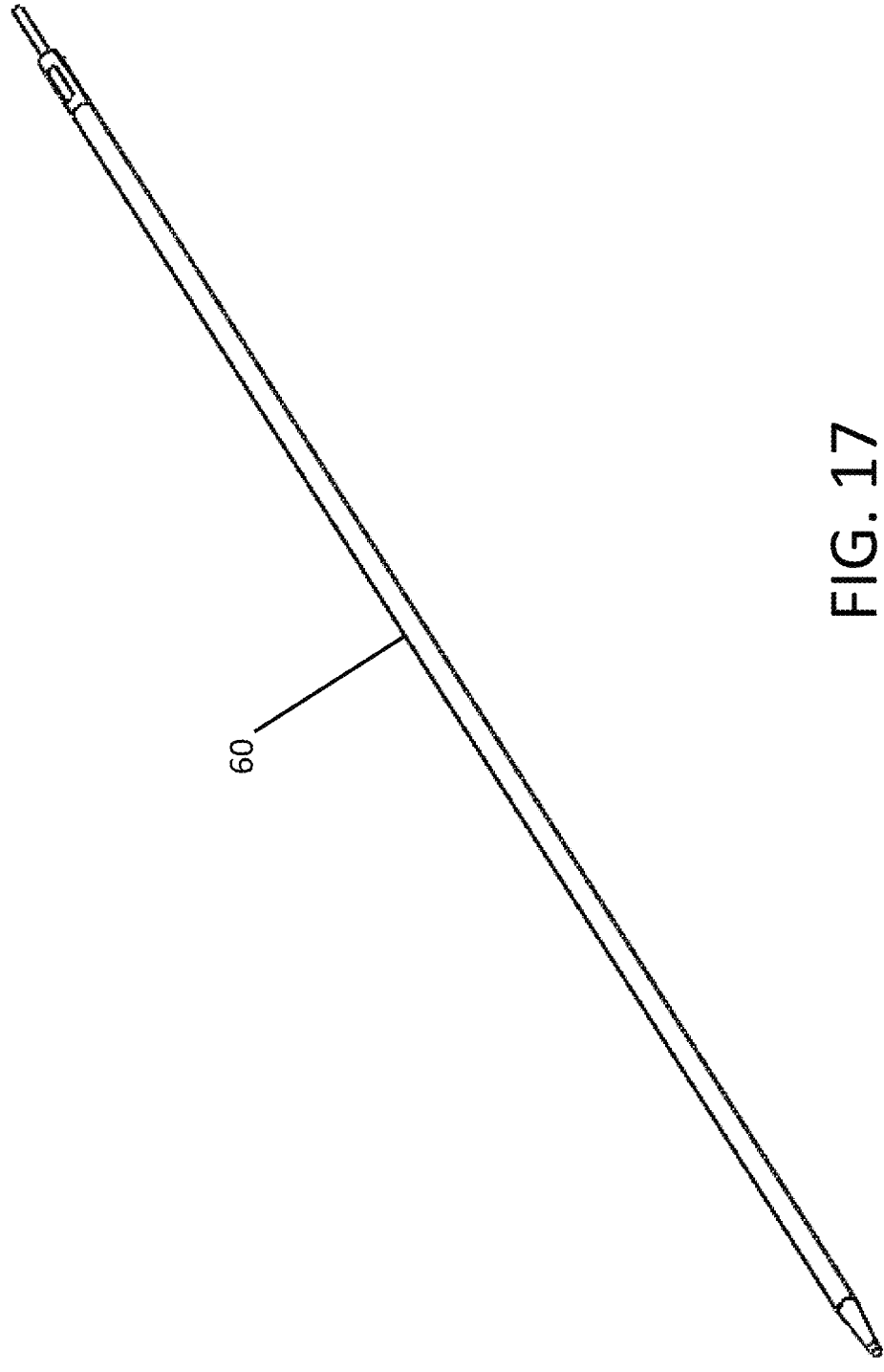
FIG. 17 is a perspective view of a neuro-monitoring dilating probe in accordance with certain embodiments of the present invention.

Once the incision has been made a neuro-monitoring dilating probe 60 (see FIG. 17) having an electrical connecter attached thereto (such as disclosed in co-pending U.S. patent application Ser. No. 16/877,087, the entirety of which is hereby incorporated herein by reference) or a monopolar probe may be used to approach the disc space. The neuro-monitoring dilating probe 60 combines four instruments into one, thereby reducing instrument exchanges and imaging requirements. Existing systems require a neuro-monitoring probe, exchange tube, guide pin and dilator to achieve the same result as the neuro-monitoring dilating probe disclosed herein.

In an embodiment using the neuro-monitoring dilating probe, an exchange tube 10 as shown in FIG. 1, having a flanged-end 12, which may be denoted by a black band or other marking, may be placed over the distal tip of neuro probe, flanged-end 12 first, until flanged end 12 contacts the probe handle.

A desirable entry location into the disc may be immediately superior to the center of the ipsilateral inferior pedicle of the motion segment to be fused. Using AP imaging, with exchange tube flange 12 flush against probe handle, the neuro-monitoring probe may be inserted and advanced through the incision until the distal tip of neuro-monitoring probe is located at the junction of the ipsilateral border of the spine and the superior endplate of the inferior vertebral body. Initially targeting this point may aid in ensuring posterior and medial passage of neuro-monitoring probe past the exiting nerve root.

As neuro-monitoring probe is advanced, an electrified tip on the neuro-monitoring probe will evoke a neural response. If at any time the technician detects a response, this is an indication that the nerve root is in, or near, the trajectory of the neuro-monitoring probe. If such a response is detected, neuro-monitoring probe may be retracted slightly, and the trajectory may be redirected to allow for continued advancement.

During identification of a safe trajectory through Kambin's Triangle, the neuro-monitoring probe trajectory may be altered slightly in multiple directions from the original trajectory in order to evoke intermittent responses. This will aid in mapping the neural structures, while also ensuring that the stimulus has not dropped below the threshold necessary to evoke a response.

When the distal tip of neuro-monitoring probe is immediately superior to the center of the ipsilateral inferior pedicle of the motion segment on an AP image, there may be a switch to lateral imaging. The neuro-monitoring probe tip may be at the junction of the posterior wall of the vertebral body and the superior endplate of the inferior vertebral body on the lateral view.

Figure 2:
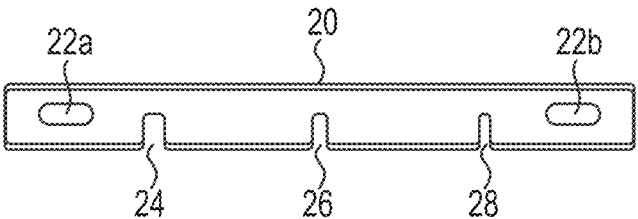
FIG. 2 is a top view of a dilator impactor in accordance with certain embodiments of the present invention.

Neural stimulation may now cease and the electrical connector may be removed from the proximal end of the neuro-monitoring probe. A dilator impactor 20, such as that shown in FIG. 2, may then be slid over the neuro-monitoring dilating probe and used to advance the neuro-monitoring dilating probe to the medial wall of the pedicle. The dilator impactor 20 may include indicator markings, such as for example, colored ends, to identify which end to slide over neuro-monitoring dilating probe.

AP imaging may be used while advancing the neuro-monitoring dilating probe to the medial wall of the pedicle. Lateral imaging may then be used to confirm that the tip of neuro-monitoring dilating probe has passed the posterior wall of the vertebral body. The neuro-monitoring dilating probe may then be advanced to the midpoint of the disc space, optionally using lateral imaging. AP imaging may then be used to confirm that the neuro-monitoring dilating probe is at the midpoint of the disc space.

Figure 18:
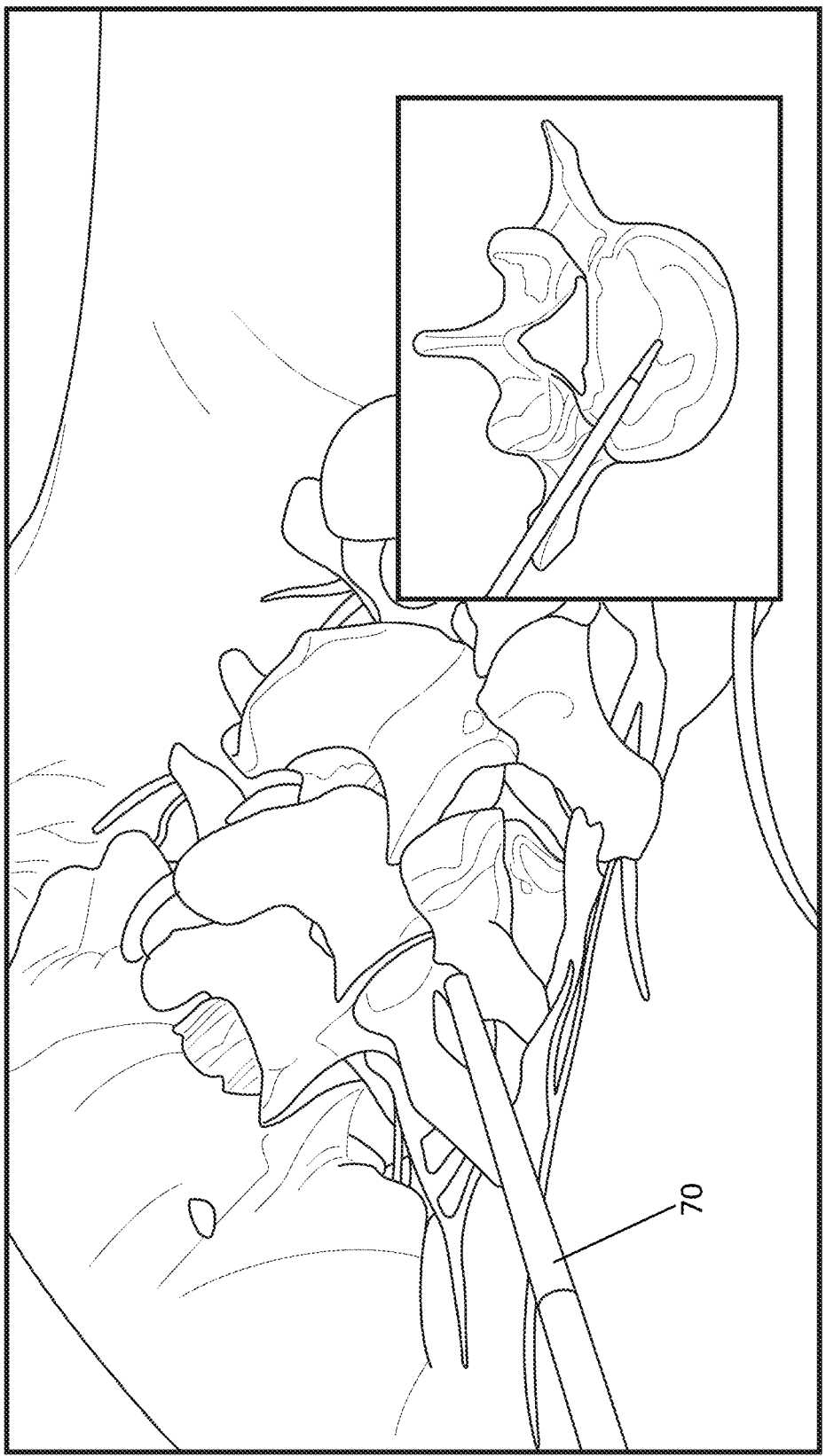
FIG. 18 is a perspective view of a second dilator in accordance with certain embodiments of the present invention.
Figures 19, 20, 21, 22:
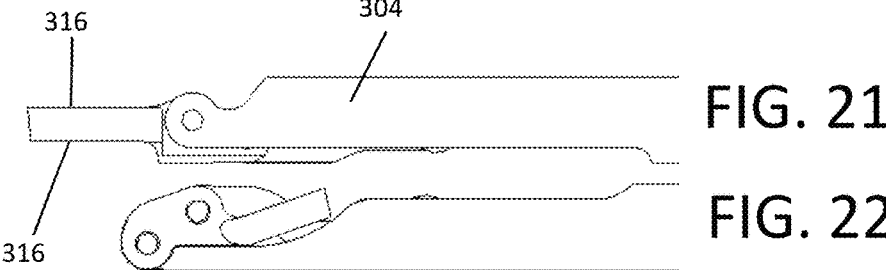
FIG. 19 is a perspective view of an articulating curette or shaper in accordance with certain embodiments of the present invention.
FIG. 20 is another perspective view of the shaper of FIG. 19 in accordance with certain embodiments of the present invention.
FIG. 21 is a side view of a distal end portion of a shaper in accordance with certain embodiments of the present invention.
FIG. 22 is another side view of a distal end portion of a shaper in accordance with certain embodiments of the present invention.
Figures 29, 30, 31, 32, 33, 34, 35:
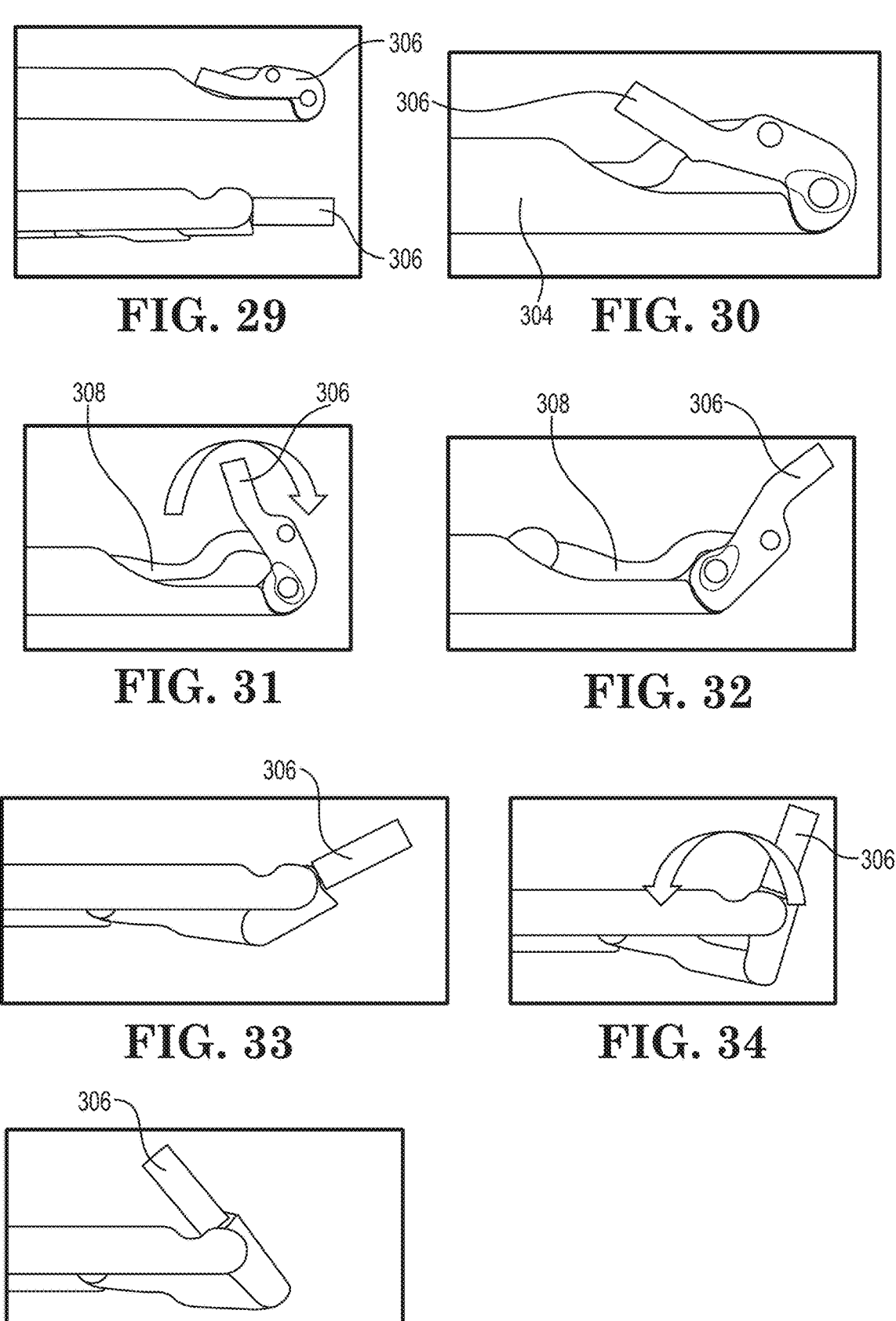
FIG. 29 is a side view of a distal end portion of a shaper in accordance with certain embodiments of the present invention.
FIG. 30 is a side view of a distal end portion of a shaper in accordance with certain embodiments of the present invention.
FIG. 31 is a side view of a distal end portion of a shaper in accordance with certain embodiments of the present invention.
FIG. 32 is a side view of a distal end portion of a shaper in accordance with certain embodiments of the present invention.
FIG. 33 is a side view of a distal end portion of a shaper in accordance with certain embodiments of the present invention.
FIG. 34 is a side view of a distal end portion of a shaper in accordance with certain embodiments of the present invention.
FIG. 35 is a side view of a distal end portion of a shaper in accordance with certain embodiments of the present invention.

A second dilator 70 (see FIG. 18) may now be passed over the neuro-monitoring dilating probe, since the neuro-monitoring dilating probe functions as a first dilator. An impactor 20 for the second dilator may be placed over the neuro-monitoring dilating probe and impacted with a mallet to advance the tip of the second dilator's tip halfway across the disc space.

In an alternate embodiment where the neuro-monitoring dilating probe is not used, a first dilator, such as monopolar probe, which is sized, dimensioned and configured the same as the neuro-monitoring dilating probe, but without the electrical connection and coating, may be used in place of the neuro-monitoring dilating probe.

Figures 3, 4, 5:
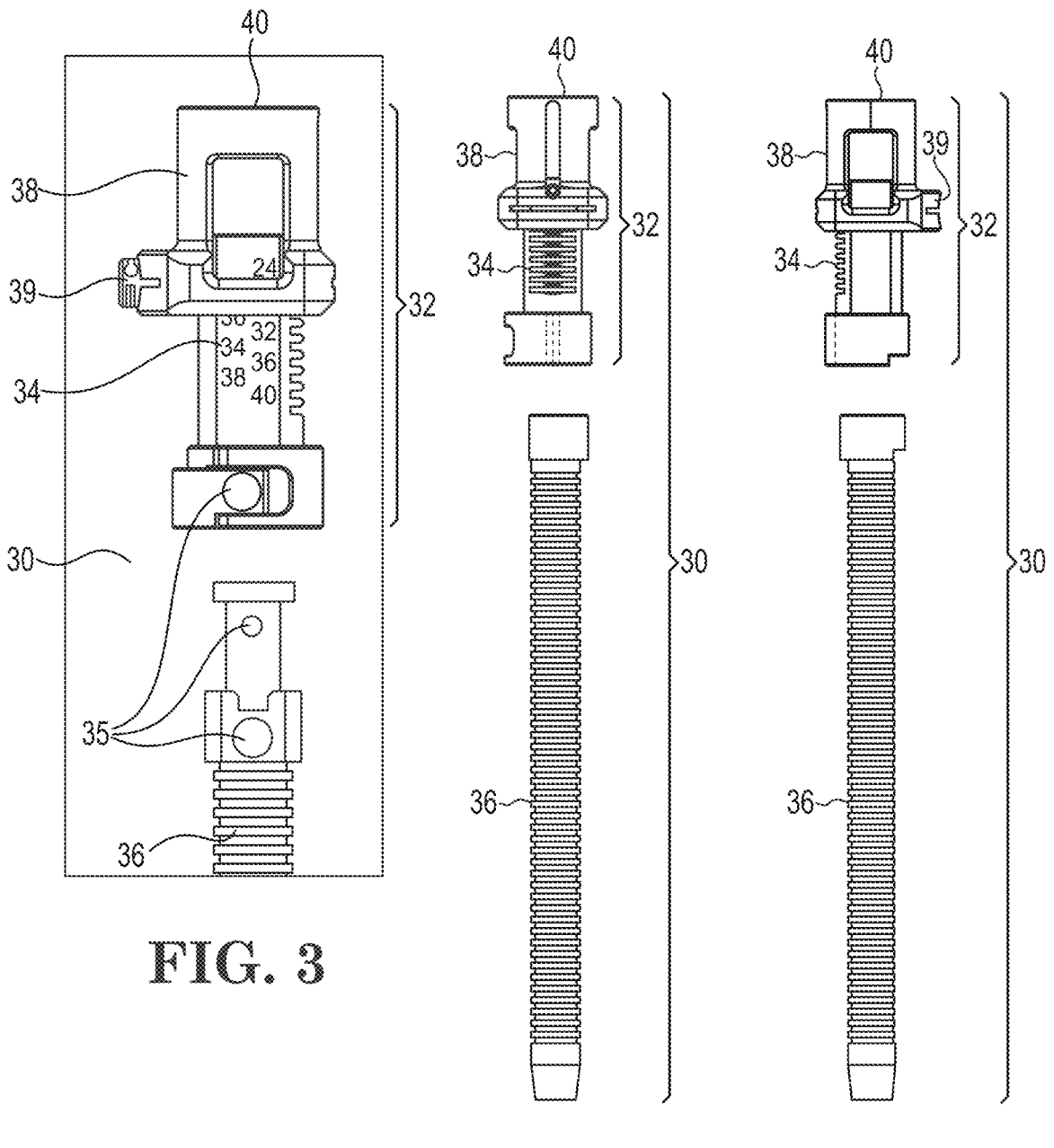
FIG. 3 is a top view of an access portal in accordance with certain embodiments of the present invention.
FIG. 4 is another top view of an access portal in accordance with certain embodiments of the present invention.
FIG. 5 is a further top view of an access portal in accordance with certain embodiments of the present invention.

Once the access to the disc space is created and the trajectory through the patient's tissues is established by using either the neuro-monitoring dilating probe and second dilator, or the first and second dilators, access portal 30, as shown in FIGS. 3-5, may be placed into the disc space.

The access portal 30 may include a portal head 32 having depth markings 34, which indicate drilling and instrument depths into the disc space. The access portal 30 may further include alignment markings 35. The access portal 30 may also include markings on stem 36 to indicate stem depth changes.

Figure 6:
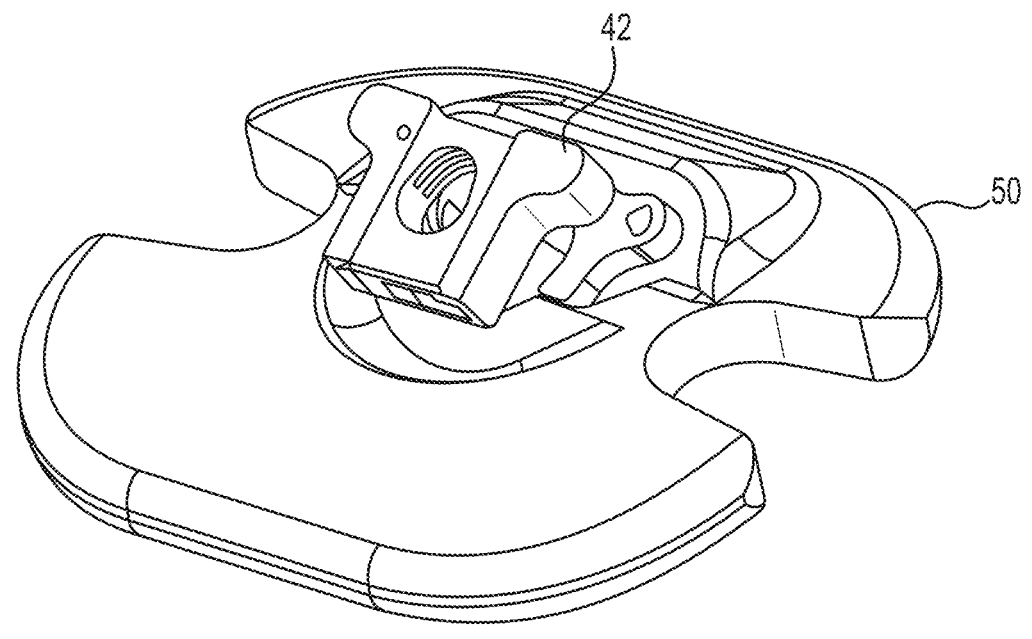
FIG. 6 is a perspective view of a force dissipation device in accordance with certain embodiments of the present invention.

The access portal 30 may be placed through an access portal lock 42 in a force dissipation device 50, such that shown in FIG. 6. In such an embodiment, the access portal 30 and the force dissipation device 50 assembly may be placed over the second dilator. An impactor may then be placed over the second dilator and into the access portal 30. According to an embodiment, a mallet may then be used to impact the impactor until the distal tip of access portal 30 is approximately 5 mm into the disc space.

In an embodiment where a force dissipation device 50 is used, force dissipation device 50 may then be advanced to the patient's skin. The second dilator may then be removed using the optional dilator impactor 20 (which also functions as a removal tool).

The dilator impactor 20 may include flats to prevent rolling, markings 22a and 22b on respective ends of the dilator impactor 20, such as for example colors to indicate which end should be used to impact the second dilator 70 or neuro monitoring dilating probe 60 and/or the first dilator. In an embodiment 22a corresponds to the second dilator and 22b corresponds to neuro-monitoring dilating probe and/or the first dilator, and multiple slots 24, 26, 28 are sized for specific dilator extraction. In an embodiment, slot 24 may be sized to extract the second dilator 2, slot 25 may be sized to extract the first dilator 1, and slot 28 may be sized to extract the neuro-monitoring dilating probe 60.

According to an embodiment, access portal 30 includes an adjustable depth stop 38 having a depth adjuster 39 to control drilling and instrument depth into the disc space. In an embodiment, once access portal 30 is placed, adjustable stop 38 may be set to a minimum, that is, the most proximal depth setting. Lateral imaging may be used to advance a drill through access portal 30 and into the disc space, rotating the drill clockwise until contact is made with access portal stop surface 40 at the proximal end of the adjustable depth stop 38.

In an embodiment, AP imaging may be taken to confirm that the drill tip is at or beyond midline. Access portal lock 42 on force dissipation device 50 may then be released to allow deeper drilling. In an embodiment, one may return to lateral imaging.

In an embodiment of the present invention the drill may be turned clockwise and monitored with fluoroscopic imaging while it is advanced to a position approximately 5 mm from the ventral margin of the disc space. The final drilling depth may be read at the base of a window in the adjustable depth stop 38.

In another embodiment, the access portal 30 may be used with a table arm support system as shown in FIGS. 8-13. The support system 100 generally comprises a vertical post member 102, a support arm 104 and a stabilizer arm 106. A bottom end of the vertical post can be provided with a clamp 108 or other fixture to secure the post to a table or other stable structure. A first adjustable arm clamp 110 is disposed around the post 102 and the support arm 104 is disposed through the first adjustable arm clamp 110. A second adjustable arm clamp 112 is disposed around the post 102 and the stabilizer arm 106 is disposed through the second adjustable arm clamp 110 adjacent a first end thereof while the opposing second end is pivotally secured to a ring support collar 114 through which the support arm 104 passes.

The unsupported end of the support arm can be provided with an attachment fixture clamp 116 that is configured to securely attach a surgical instrument or a fixture for a surgical instrument.

Each of the first arm clamp 110 and second arm clamp 112 are provided with a locking adjustment knob 118 that the user can loosen to adjust the respective members 104, 106 in many different directions and degrees of freedom as can be appreciated from the figures. The clamps 110, 112 can also be disposed over the post 102 in an inverted direction (or the members 104, 106 inserted in an opposite direction) so that the knobs 118 are facing the opposite direction as may be desired.

An indexing rod 120 can be secured to each of the first 110 and second 112 clamps to ensure consistent spacing, and thus consistent support provided to the support arm 104 by the stabilizer arm. The indexing rod also functions to index the clamps 110, 112 so that assembly is simplified.

The ends of the arms 104, 106 can be configured with spring-loaded engagement members 122 in order to snap the arm ends securely into their respective clamps 110, 112. The spring members 122 prevent the arms 104, 106 from accidentally slipping out of their clamps during adjustment or assembly/disassembly.

Figure 13:
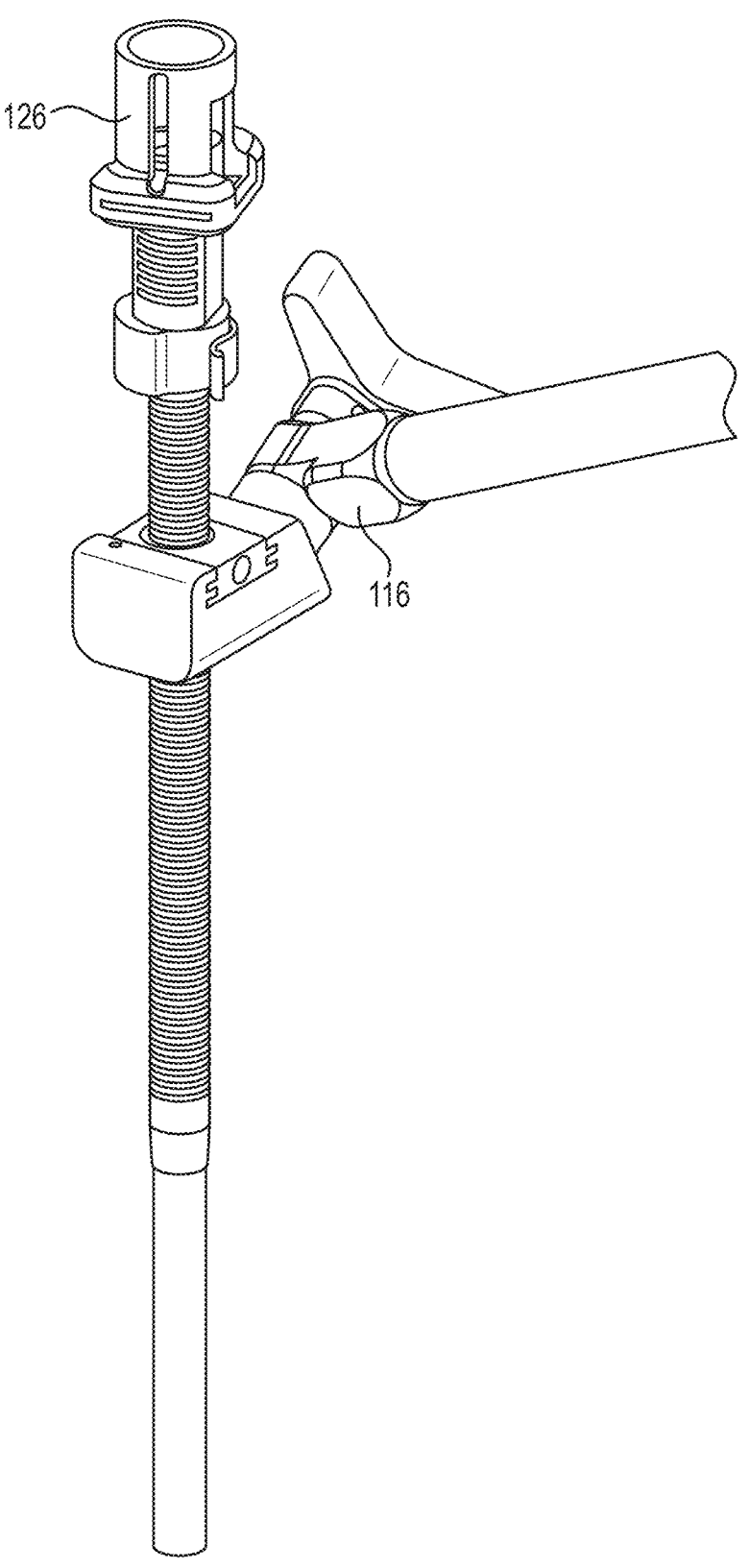
FIG. 13 is a perspective view of a fixture disposed in a fixture clamp of the table arm support system of FIG. 8 in accordance with certain embodiments of the present invention.

One type of attachment for fixture clamp 116 that can be used with the present system is shown in FIG. 13. The depicted fixture 126 is a conical interfaced instrument nest. Of course, other types of fixtures can be used instead.

A top knob 124 can be provided to the post 102 so that the user can turn the knob to tighten and loosen the clamp 108 of the post 102.

An expandable reamer or shaper (such as disclosed in U.S. Pat. No. 6,383,188, the entirety of which is incorporated by reference herein) may be used to facilitate the discectomy and to remove cartilage from the endplates. The shaper may be passed through access portal 30 until shaper body contacts access portal stop surface 40 to position Shaper blades at the distal end of the cavity. The shaper blades may be opened incrementally by turning a blade control knob one turn. The shaper may be rotated with the drive knob while moving shaper along the entire track made by the drill. The process of incrementally opening the blades while monitoring with lateral or oblique imaging until the blade tips touch the endplates, may be repeated as desired to remove disc material.

The access portal 30 may be moved medial-lateral as needed to broaden the cavity created by the shaper.

Disc material and cartilage loosened by the shaper may be removed by using a pituitary rongeur and irrigation/suction. The suction tube may include a marking, such as for example, a band to indicate when the suction tube has reached the end of the access portal.

In an embodiment of the present invention, articulating curettes may be used to broaden the cavity created by the shaper and decorticate the vertebral body endplates. The articulating curettes may include hubs which may contact access portal stop to control and vary the placement depth into the disc space.

According to an embodiment, an articulating curette and/or a reverse articulating curette (such as is disclosed in co-pending U.S. patent application Ser. No. 17/027,619, filed Sep. 21, 2020, which is incorporated herein by reference in its entirety) may be used. Referring to FIGS. 19-39, the shaper or articulating curette 300 may cut with the blade 106 swinging distal to proximal, while the main shaft 104 to which the blade is pivotally secured rotates 180 degrees by an adjustment handle 102 so that the cutting blade is inverted to move in the reverse direction. This reversibility eliminates the need to rotate the curette 180 degrees. The reverse articulating curette 300 may cut with the blade 106 swinging proximal to distal, articulating away from the handle 102, which allows for removing tissue close to the end of access portal 30. When both are used, they cut a complete 360 degree circular area, reaching approximately 13 mm one way from the center line to create a total cavity of approximately 26 mm.

Referring to FIGS. 19-39, the articulating curette 300 (also referred to as a shaper) generally comprises a handle assembly 302 disposed on a proximal end of a hollow main shaft 304 and a cutting tip 306 pivotally disposed at the distal end of the main shaft 304. A channel 305 can be formed longitudinally through the main shaft 304.

A distal end of an actuator shaft 308 is coupled to an end of the cutting tip 306 opposite the cutting edge thereof. The proximal end of the actuator shaft 308 is coupled to a cutting actuator handle 310 of the handle assembly 302. The actuator shaft 308 extends longitudinally through the main shaft 304.

The main shaft 304 is rotationally coupled to the handle assembly so that the main shaft 304 can rotate 180 degrees about its longitudinal axis. A rotation actuator handle 312 is disposed in a curved slot 309 located adjacent to a distal end of the handle assembly 302 and is coupled to the main shaft 304. Thus, the handle 312 can be used by the operator to selectably rotate the main shaft 304 up to 180 degrees from a normal (or first) orientation (FIG. 19) to an inverted (or second) orientation (FIG. 20) that is 180 degrees opposite that of the normal orientation. FIGS. 36-37 show the handle 312 in the normal position and the inverted position, respectively.

The stem 313 or distal end of the rotation actuator handle 312 (opposite the proximal or bulbous end that the user can grasp) mates with a correspondingly-shaped recess 314 defined in the curved slot 309 slot through which the rotation actuator handle 312 moves. This ensures that the shaft 304 does not unintentionally rotate. A similar recess is also defined at the fully-inverted position so that the rotation actuator handle 312 is secured in the inverted position.

The stem 313 can comprise a spring loaded lockout mechanism. This feature requires the user to pull axially on the stem 313 of the handle 312 in the proximal direction towards an end stop 315 to disengage the stem 313 from the recess 314 before the handle 312 can be rotated. This locking mechanism configuration further prevents the main shaft 304 from unintentionally rotating.

The slot 309 can be configured with additional recesses 314 to provide for more than the depicted two recesses arrayed 180 degrees opposite one another. For example, a third slot can be placed at 90 degrees offset from the first rotational position. The slot 309 can sized to allow for more than 180 degrees of rotation of the main shaft 304 (e.g. 270 or 360 degrees of rotation). The slot 309 can also be sized to allow for less than 180 degrees of rotation of the main shaft 304 (e.g. 90 degrees of rotation).

The cutting tip 306 has a cutting edge 316 defined on one or both of the top and bottom sides thereof. The two-sided configuration (shown throughout the figures) allows the cutting tip 306 to cut using both the forward and reverse rotational directions. Note that FIGS. 27-28 and 39 show the cutting tip with the main shaft 304 rotated into the inverted position.

In use, the user inserts the distal end of the shaper 300 into the target location in the patient's tissues such that the cutting tip 306 is in the desired location to remove tissue. Then the cutting actuator handle 318 is actuated to pivot and move the cutting tip 306 forward to create a first half-circle portion of a cavity in the patient's tissues. Next, the user pulls proximally on the handle 312 in an axial direction to release the rotation actuator handle 312 from its recess 314. Then the user rotates the rotation actuator handle 312 to the desired position (e.g., the inverted position) so that the cutting tip 306 pivots in the reverse direction to remove the second half-circle portion of a cavity in the patient's tissues. The result is that a complete or substantially complete circular or arcuate cavity is formed such as is desired in a discectomy procedure.

The spring or resilient member inside of the stem 313 of the rotation actuator handle 312 automatically pulls the handle 312 axially downward in its distal direction into the respective recess 314 and maintains the handle 312 there until the user pulls the handle 312 with sufficient force to initiate a deliberate rotational movement of the main shaft 304.

The two-sided cutting tip 306 and ability to rotate the tip 306 from a normal to an inverted position allows the user to easily invert the cutting tip, without rotating the actuator handle 310 of the handle assembly 302 itself, by rotating the main shaft 180 degrees so that the remaining half-circle of tissue can be removed for a complete discectomy.

Tissue extractor brushes may be used to remove tissue located at the cavity periphery. Tissue extractor brushes may be inserted through access portal 30. The tissue extractor brush may be rotated inside the disc space while moving medial-lateral and anterior-posterior as needed to remove disc material. This process may be repeated until tissue extractor brushes are removed from access portal 30 without disc material in the bristles.

Figures 14, 15:
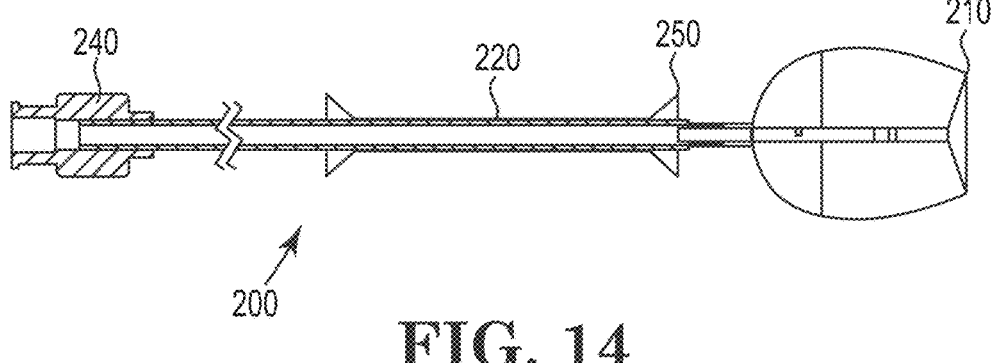
FIG. 14 is a top view in longitudinal cross-section of a discectomy verification device in accordance with certain embodiments of the present invention.
FIG. 15 is a top view of a discectomy verification device in accordance with certain embodiments of the present invention.
Figure 16:
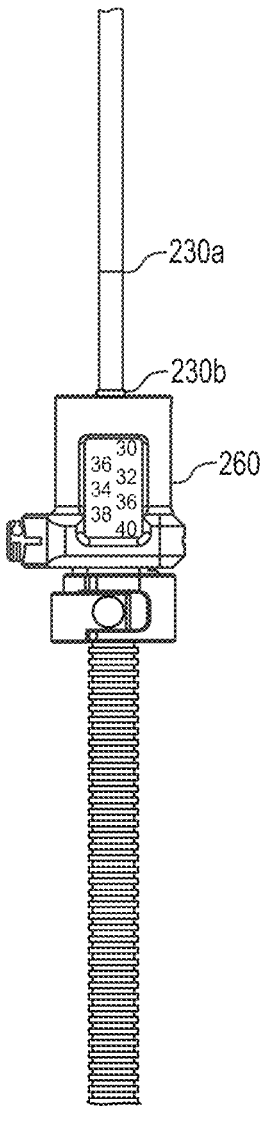
FIG. 16 is a partial top view of discectomy verification device coupled to a depth stop in accordance with certain embodiments of the present invention.

In an embodiment of the present invention, a discectomy verification device may be used. An example embodiment of such device is shown in FIGS. 14-16. The discectomy verification device 200 comprises an expandable and/or inflatable device 210, such as for example a balloon catheter, which is operably engaged to a distal end of a cannula 220. In one embodiment, the discectomy verification device 200 may be comprised of a polyurethane, other biocompatible materials are contemplated.

The cannula 220 may include a luer lock 240 having a stopcock or other feature configured to receive a syringe or other fluid delivery system. In an embodiment, luer lock 240 may include a cap to the open portal of the stopcock to prevent inadvertent release of contrast medium. The cannula 20 may include markings 230 on its proximal end. The marking 230 may have a proximal edge 230*a* and a distal edge 230*b*. Markings 230 may be used to indicate depth of insertion into a patient.

The discectomy verification device 200 may be inserted through the portal that has been placed into the intervertebral disc space. As can be seen in FIG. 16, markings 230*a* and 230*b* may be coupled to a depth stop 260, scale or other indicator such that the depth of insertion may be determined visually by the markings 230. When the proximal mark edge 230*a* is aligned with the top edge of the depth stop 260 of the access portal this indicates that the discectomy verification device 200 is in a position at a shortest depth marking on the portal. When the distal mark 230*b* is aligned with the top edge of the depth stop 260 the discectomy verification device 200 is in a position of deepest depth into the cavity. Markings 230 eliminate the need to image to ensure proper placement in the disc space.

The cannula 220 may further include flare 250 a flange or other feature to protect the discectomy verification device 200 upon insertion into the patient.

In use, the inflatable device 210 of the discectomy verification device 200 is inserted into a patient's intervertebral disc cavity after the disc material has been removed. A syringe or other fluid delivery device may be attached to the cannula 210 such that contrast medium may be delivered through the cannula 220 and into inflatable device 210 such that the inflatable device inflates to conform to the shape of the cavity. The contrast medium may then be seen on imaging such that the surgeon may evaluate the disc cavity created to determine whether the discectomy is thorough. For example, lateral and/or AP images may be taken to view the size and shape of the discectomy cavity. Based on the images and desired discectomy use of the discectomy instruments may be repeated until a complete discectomy is obtained.

In another embodiment, the inflatable device 210 may be inflated prior to disc material removal to visualize the cavity prior to the discectomy. In yet another embodiment, the inflatable device 210 may be inflated and removed repeatedly to continue checking on the state of the disc cavity.

Figure 7:
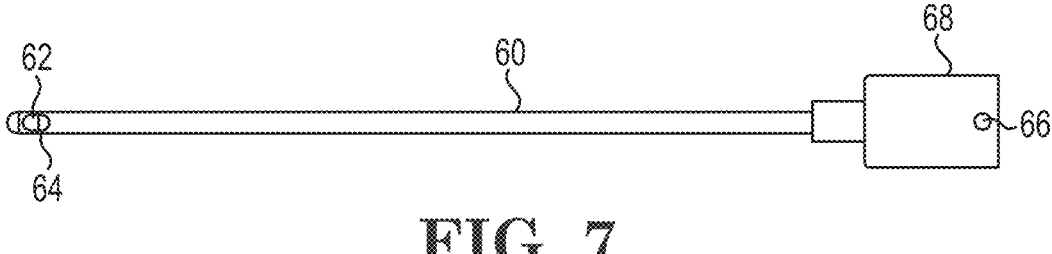
FIG. 7 is a top view of a graft delivery tool in accordance with certain embodiments of the present invention.
Figure 8:
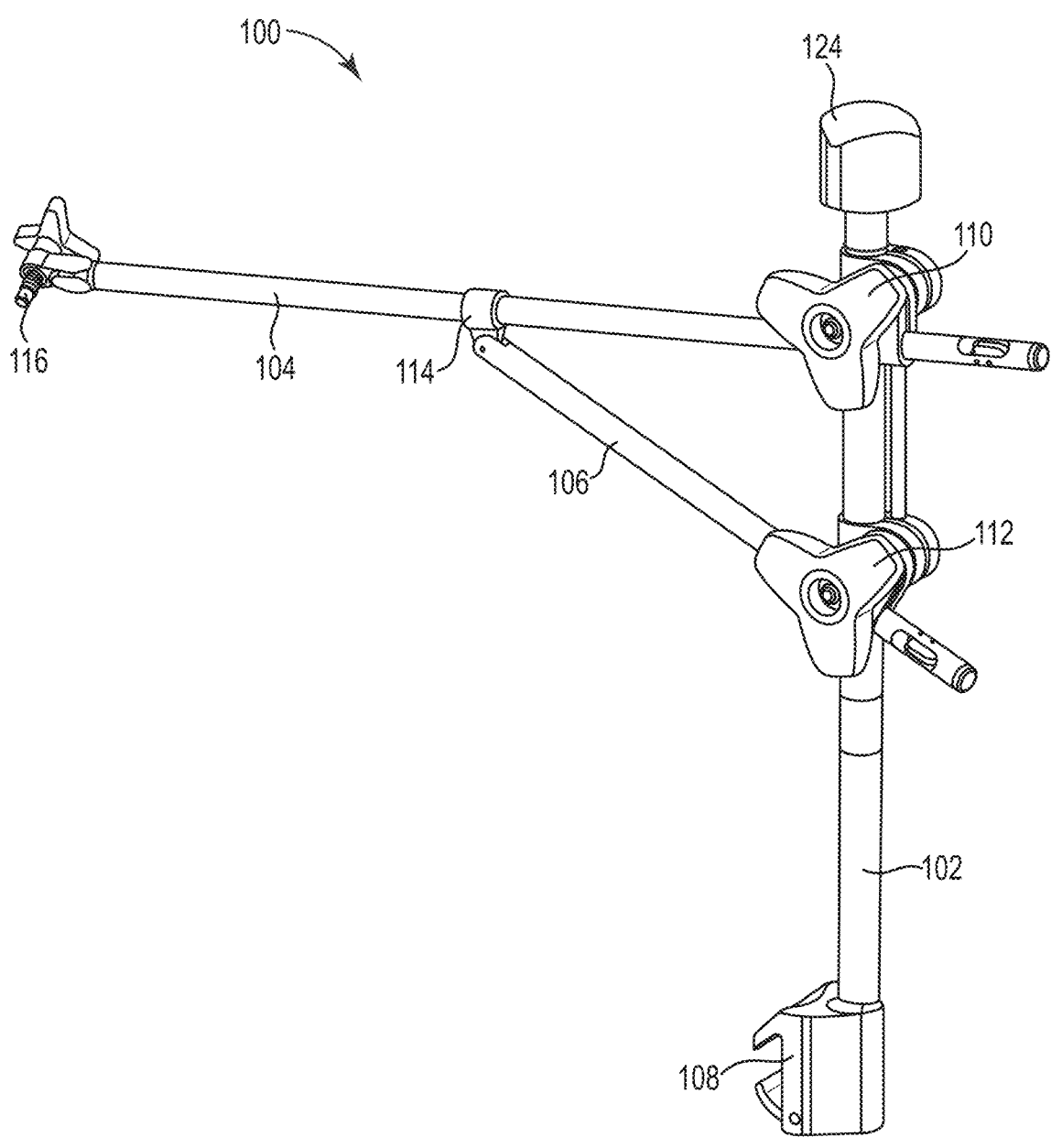
FIG. 8 is a perspective view of a table arm support system in accordance with certain embodiments of the present invention.
Figure 9:
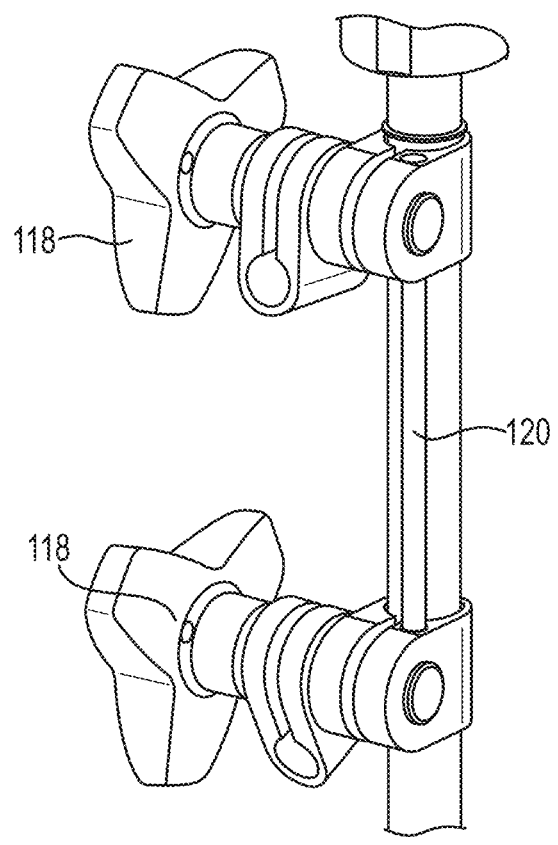
FIG. 9 is a perspective view of a portion of the table arm support system of FIG. 8 in accordance with certain embodiments of the present invention.
Figure 10:
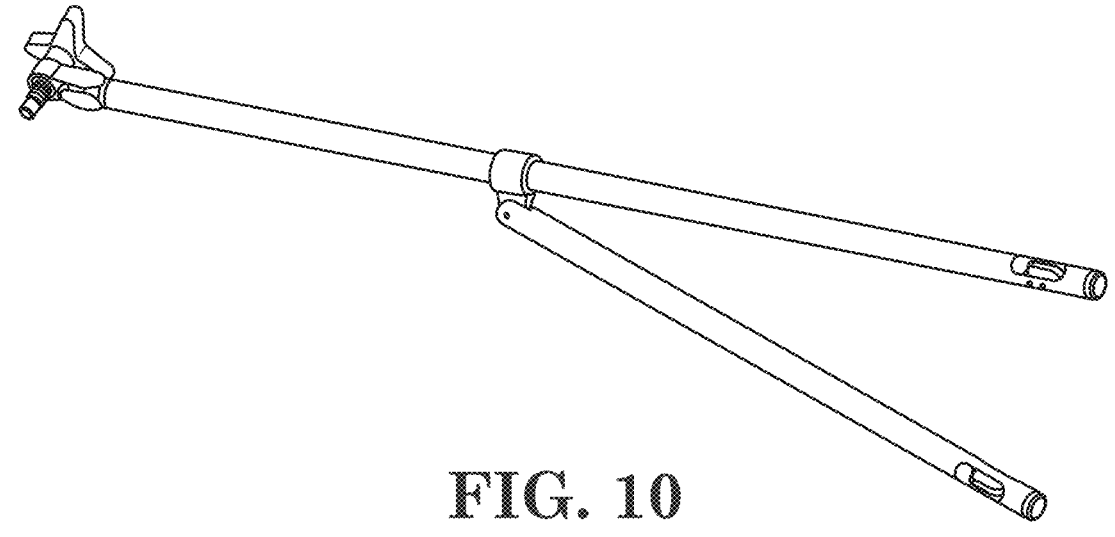
FIG. 10 is a perspective view of a support arm of the table arm support system of FIG. 8 in accordance with certain embodiments of the present invention.
Figure 11:
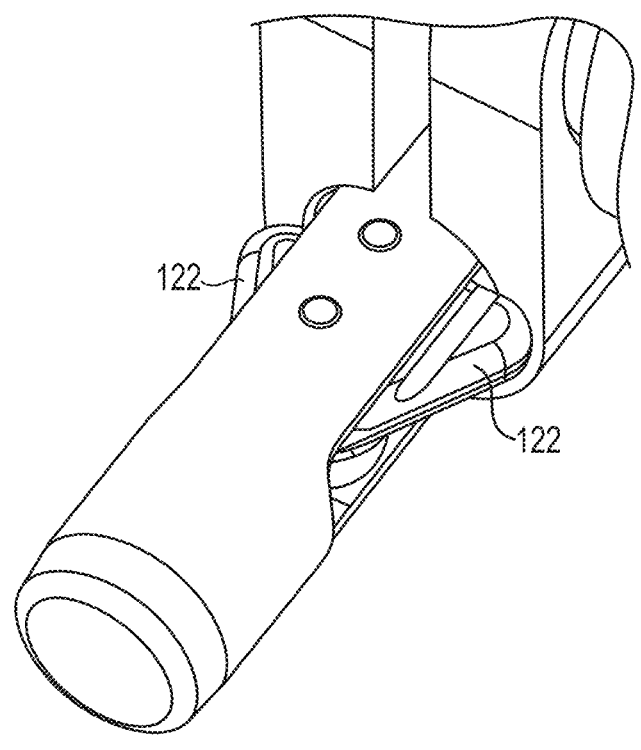
FIG. 11 is a perspective view of a portion of the support arm of FIG. 10 in accordance with certain embodiments of the present invention.
Figure 12:
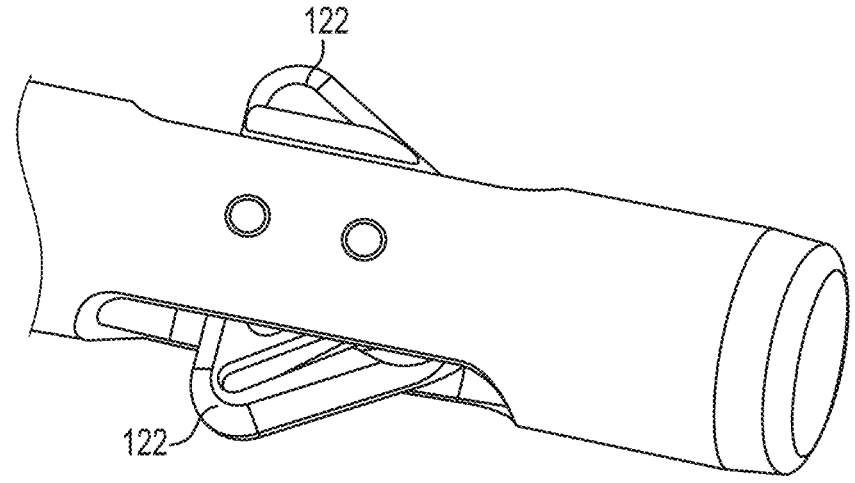
FIG. 12 is another perspective view of a portion of the support arm of FIG. 10 in accordance with certain embodiments of the present invention.

Once a complete discectomy is achieved, bone graft and/or an implant may be placed into the intervertebral cavity. In an embodiment, as can be seen in FIG. 7, a graft delivery instrument 60 may be filled with re-hydrated cortical fibers or any other bone graft or fill material. The graft delivery instrument 60 may be placed through access portal 30. The bone graft or other desired biocompatible material may be expelled parallel to the endplates using a push rod. The graft delivery instrument 60 may include dual discharge ports 62, 64, each opening to opposing sides of instrument 60 to disperse graft on both sides of the disc cavity, and holes 66 at the top of a graft tube reservoir 68 to aid in the proper orientation of the openings at the distal end of graft delivery instrument 60.

In an embodiment, an intervertebral implant may be placed in the prepared cavity. A percutaneous implant guide, such as is disclosed in US Patent Application Publication No. 2019/0240044, which is hereby incorporated by reference in its entirety herein, may be used to facilitate placing the implant. In another embodiment, a percutaneous fusion may be performed according to the disclosure in U.S. Pat. No. 8,906,094, which is hereby incorporated by reference in its entirety herein.

Any two or more of the instruments disclosed herein can be packaged as part of a kit and system. The kit and system can also include a spinal implant. The kit and system embodiments can also include additional surgical instruments not mentioned herein. The kit and system can be enclosed together in a case, container or enclosure.

Features of the various embodiments can be mixed and matched to create additional embodiments even if not specifically depicted in one of the figures.

The present invention may be embodied in other specific forms without departing from the spirit or essential attributes thereof, and it is, therefore, desired that the present embodiment be considered in all respects as illustrative and not restrictive. Those skilled in the art may recognize other equivalents to the specific embodiment described herein which equivalents are intended to be encompassed by the claims attached hereto.

What is claimed is:

1. A method of performing percutaneous spinal interbody fusion on a spine of a patient, the method comprising:
   inserting without direct visualization a neuro-monitoring dilating probe into the patient;
   advancing the neuro-monitoring dilating probe into a disc space;
   removing tissue from the patient using an articulating curette, wherein the step of removing tissue from the patient using an articulating curette comprises:
      pivoting a cutting head of the articulating curette in a first rotational direction to remove tissue from the patient; and
      rotating a main shaft of the articulating curette with respect to a handle assembly of the articulating curette so that the cutting head will be inverted and rotate in a second rotational direction opposite the first rotational direction to remove tissue from the patient.

2. The method of claim 1, further comprising:
   passing a second dilator over the neuro-monitoring dilating probe; and
   advancing the second dilator into the disc space.

3. The method of claim 2, further comprising:
   placing an impactor over the second dilator;
   placing an access portal into the disc space; and
   impacting the impactor until a distal tip of an access portal is penetrated into the disc space.

4. The method of claim 3, further comprising removing the second dilator using the dilator impactor.

5. The method of claim 3, further comprising advancing a drill through the access portal until the drill contacts an access portal stop surface of an adjustable stop of the access portal.

6. The method of claim 3, further comprising placing a force dissipation device over the second dilator, wherein the access portal is placed through an access portal lock of the force dissipation device.

7. The method of claim 3, further comprising adjusting a depth stop of the access portal to define a permissible depth that a surgical instrument can penetrate into the patient.

8. The method of claim 1, further comprising placing an implant in a prepared cavity in the disc space via a percutaneous implant guide.

9. The method of claim 1, further comprising performing neuro-monitoring via the neuro-monitoring dilating probe.

10. The method of claim 1, further comprising removing material from the disc space via a shaper instrument.

11. A method of performing percutaneous spinal interbody fusion on a spine of a patient, the method comprising:
   inserting without direct visualization a neuro-monitoring dilating probe into the patient;
   advancing the neuro-monitoring dilating probe into a disc space;
   inflating an expandable device of a discectomy verification device with contrast medium when the expandable device is located inside of the disc space.

12. The method of claim 11, further comprising, when the expandable device is inflated with the contrast medium inside of the disc space, performing indirect visualization imaging of the disc space to view a size and a shape of the disc cavity.

13. The method of claim 11, further comprising determining a depth of insertion of the discectomy verification device by comparing a visual marking on the discectomy verification device to a depth stop of an access portal.

14. The method of claim 11, further comprising placing an implant in a prepared cavity in the disc space via a percutaneous implant guide.

15. The method of claim 11, further comprising performing neuro-monitoring via the neuro-monitoring dilating probe.

16. The method of claim 11, further comprising:
passing a second dilator over the neuro-monitoring dilating probe; and
advancing the second dilator into the disc space.

17. The method of claim 16, further comprising:
placing an impactor over the second dilator;
placing an access portal into the disc space; and
impacting the impactor until a distal tip of an access portal is penetrated into the disc space.

18. A method of performing percutaneous spinal interbody fusion on a spine of a patient, the method comprising:

inserting without direct visualization a neuro-monitoring dilating probe into the patient;
advancing the neuro-monitoring dilating probe into a disc space;
passing a second dilator over the neuro-monitoring dilating probe;
placing an access portal into the disc space; and
placing a force dissipation device over the second dilator, wherein the access portal is placed through an access portal lock of the force dissipation device.

19. The method of claim 18, further comprising removing tissue from the patient using an articulating curette.

20. The method of claim 19, wherein the step of removing tissue from the patient using an articulating curette comprises:
pivoting a cutting head of the articulating curette in a first rotational direction to remove tissue from the patient; and
rotating a main shaft of the articulating curette with respect to a handle assembly of the articulating curette so that the cutting head will be inverted and rotate in a second rotational direction opposite the first rotational direction to remove tissue from the patient.

* * * * *